(12) United States Patent
Terashita

(10) Patent No.: US 9,945,796 B2
(45) Date of Patent: Apr. 17, 2018

(54) X-RAY FLUORESCENCE ANALYSIS METHOD AND X-RAY FLUORESCENCE ANALYSIS SYSTEM

(71) Applicant: SHIMADZU CORPORATION, Kyoto-shi, Kyoto (JP)

(72) Inventor: Eisaku Terashita, Kyoto (JP)

(73) Assignee: SHIMADZU CORPORATION, Kyoto-shi (JP)

(*) Notice: Subject to any disclaimer, the term of this patent is extended or adjusted under 35 U.S.C. 154(b) by 98 days.

(21) Appl. No.: 15/027,262

(22) PCT Filed: Oct. 15, 2013

(86) PCT No.: PCT/JP2013/078001
§ 371 (c)(1),
(2) Date: Apr. 5, 2016

(87) PCT Pub. No.: WO2015/056304
PCT Pub. Date: Apr. 23, 2015

(65) Prior Publication Data
US 2016/0258887 A1    Sep. 8, 2016

(51) Int. Cl.
G01N 23/223    (2006.01)
(52) U.S. Cl.
CPC ................. *G01N 23/223* (2013.01)
(58) Field of Classification Search
CPC .............. G01N 23/223; G01N 2223/076
USPC .......................... 378/44–50, 86–90
See application file for complete search history.

(56) References Cited

U.S. PATENT DOCUMENTS

2006/0274882 A1* 12/2006 Kawahara ............ G01N 23/223
378/45
2009/0041184 A1* 2/2009 Kawahara ............ G01N 23/223
378/45

FOREIGN PATENT DOCUMENTS

JP        8-334481 A     12/1996
JP      2010-223908 A    10/2010

OTHER PUBLICATIONS

Written Opinion for PCT/JP2013/078001 dated Jan. 28, 2014. [PCT/ISA/237].

(Continued)

*Primary Examiner* — Courtney Thomas
(74) *Attorney, Agent, or Firm* — Sughrue Mion, PLLC

(57) ABSTRACT

An X-ray fluorescence analysis method in which the quantity of a contained component other than the principal component in the sample is determined by using the result of measurement of X-rays emitted from a sample whose principal component is an organic component, includes: setting a quantitative value of the contained component; calculating an area occupancy ratio representing the proportion of X-rays falling onto the sample; recalculating the area occupancy ratio based on a comparison of a measured value of the scattered X-ray intensity with a theoretical value of the scattered X-ray intensity calculated using a recalculated quantitative value of the contained component and the area occupancy ratio; repeating the recalculation of the quantitative value of the contained component and the recalculation of the area occupancy ratio, and determining the quantitative value as the definite quantitative value of the contained component when the quantitative value satisfies a previously set convergence condition.

2 Claims, 3 Drawing Sheets

(56) References Cited

OTHER PUBLICATIONS

International Search Report for PCT/JP2013/078001 dated Jan. 28, 2014.

* cited by examiner

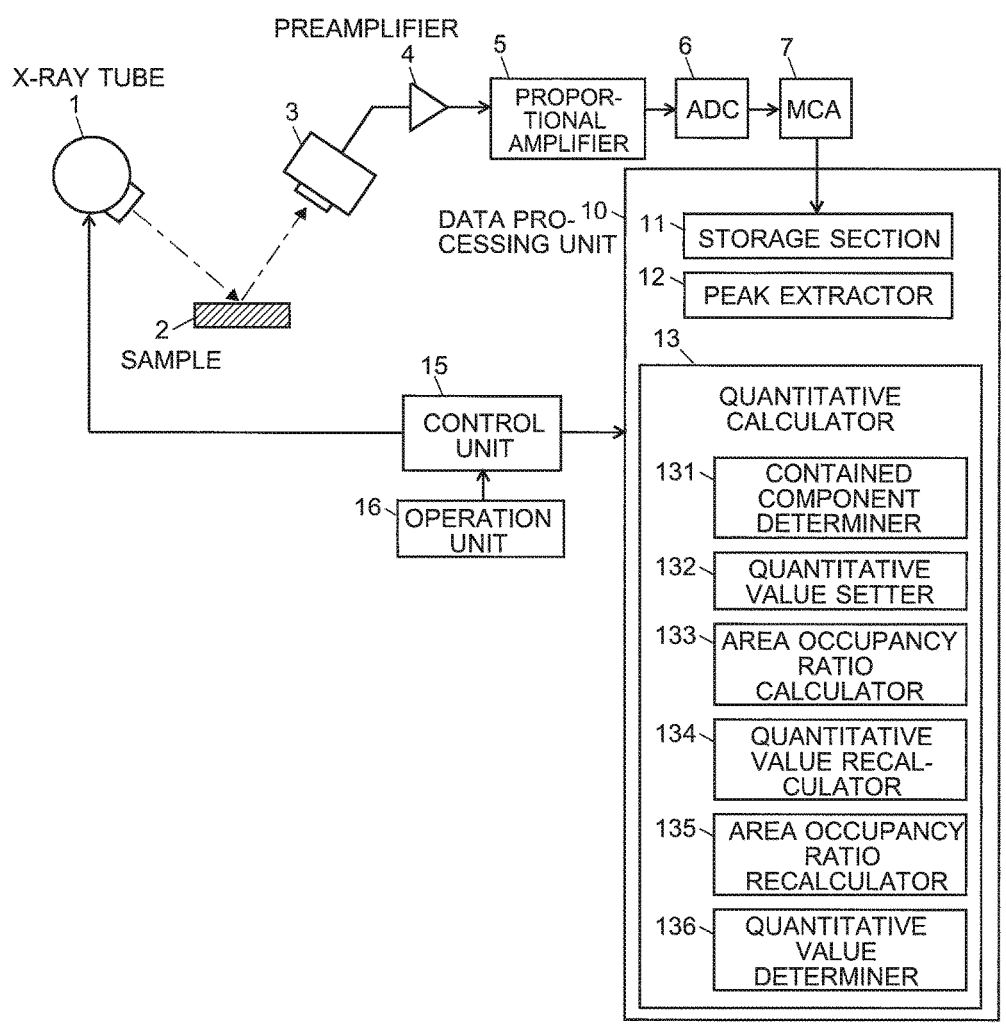

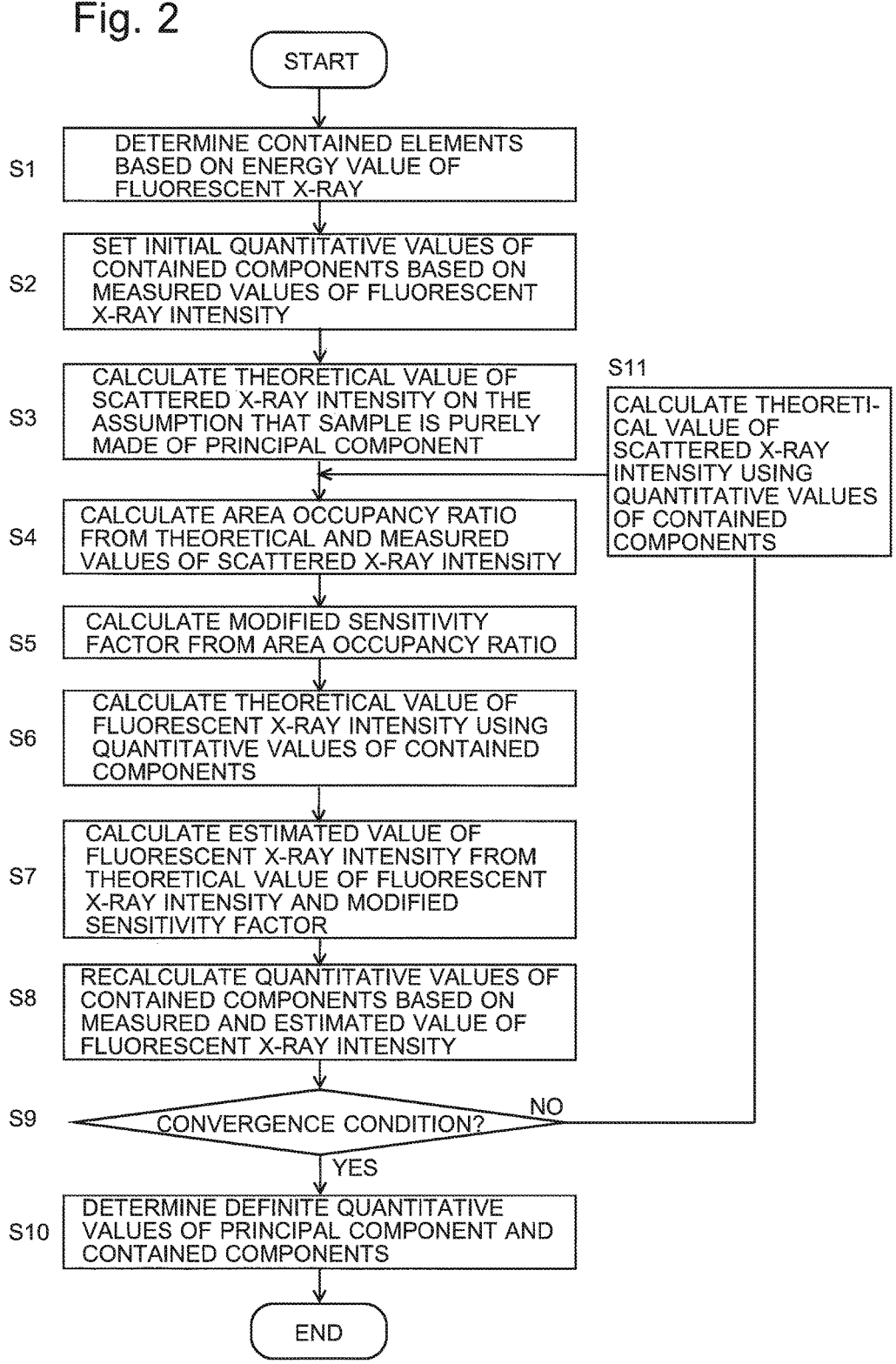

Fig. 3A
SAMPLE A
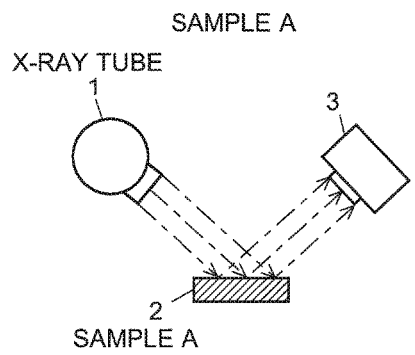
Fig. 3B
SAMPLE B
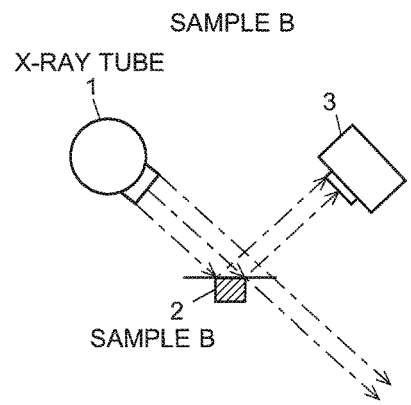
Fig. 4
|  | Sample 1 (Entire Surface) | | Sample 2 (One Half) | | |
|---|---|---|---|---|---|
|  | Fluorescent X-ray Intensity | Quantitative Value (%) | Fluorescent X-ray Intensity | Quantitative Value (%) (Not Corrected) | Quantitative Value (%) (Corrected) |
| Br | 138.8984 | 0.053 | 43.0440 | 0.014 | 0.046 |
| Hg | 43.3648 | 0.041 | 12.5840 | 0.013 | 0.041 |
| Pb | 34.1020 | 0.040 | 14.9965 | 0.012 | 0.040 |
| Cr | 25.4891 | 0.036 | 9.2423 | 0.011 | 0.037 |
| Cu | 6.8611 | 0.003 | 0.9441 | 0.001 | 0.002 |
| Fe | 2.2632 | 0.002 | 1.2106 | 0.000 | 0.002 |
| Zn | 3.0994 | 0.002 | 0.9947 | 0.000 | 0.001 |
| Resin (Principal Component) |  | 99.824 |  | 99.949 | 99.832 |

X-RAY FLUORESCENCE ANALYSIS METHOD AND X-RAY FLUORESCENCE ANALYSIS SYSTEM

CROSS REFERENCE TO RELATED APPLICATIONS

This application is a National Stage of International Application No. PCT/JP2013/078001 filed Oct. 15, 2013, the contents of which are incorporated herein by reference in their entirety.

TECHNICAL FIELD

The present invention relates to an X-ray fluorescence analysis method and system in which a sample is irradiated with excitation X-rays and the fluorescent X-rays emitted from the irradiated sample in response to the irradiation are monitored to determine the quantities of sample components. Specifically, it relates to an X-ray fluorescence analysis method and system which perform the quantitative determination of sample components by using a fundamental parameter method (which is hereinafter called the "FP method").

BACKGROUND ART

The X-ray fluorescence analysis method is used to identify the kinds of minor components (e.g. metallic elements) contained in a resin product or foodstuff and determine their quantities. The kinds of minor components are identified from the energy of the detected fluorescent X-rays, while their quantities are determined from the intensity of the fluorescent X-rays.

The FP method is one of the methods for the quantitative determination of sample components (for example, see Patent Literatures 1 and 2). Unlike the calibration curve method which requires the task of previously creating a calibration curve by performing measurements on a large number of standard samples composed of similar substances to the measurement target sample at different concentrations, the FP method does not require such a task and therefore is suitable for an analysis of a sample containing unknown kinds of components.

In the FP method, the content of each component is determined from a measured value of the intensity of the fluorescent X-rays by means of a theoretical formula for calculating the intensity of the fluorescent X-rays. However, no fluorescent X-rays can be detected from organic substances. Therefore, as in the case of resin products, when the principal component is an organic substance, the quantitative value of the principal component is determined by subtracting, from the entire quantity, the previously determined quantitative values of the components other than the principal component.

CITATION LIST

Patent Literature

Patent Literature 1: JP 08-334481 A
Patent Literature 2: JP 2010-223908 A

SUMMARY OF INVENTION

Technical Problem

The theoretical calculation performed in the FP method premises that the entire amount of X-rays cast onto the X-ray irradiation window of the sample chamber fall onto the sample. To this end, the analysis is performed with the sample shaped so as to entirely cover the X-ray irradiation window. However, when the sample does not allow such a shaping (as in the case of a linearly shaped resin product), only a portion of the cast X-rays falls onto the sample. Therefore, the intensity of the fluorescent X-rays emitted from such a sample will be lower than that of the fluorescent X-rays which would be emitted if the same sample were shaped so as to entirely cover the X-ray irradiation window, with the result that the quantity of the sample component theoretically calculated by the comparison with the measured value of the intensity will be lower than the actual quantity of the component.

The problem to be solved by the present invention is to provide an X-ray fluorescence analysis method and system capable of accurately determining the quantity of a component in a sample without being affected by the shape of the sample.

Solution to Problem

The present invention developed for solving the previously described problem is an X-ray fluorescence analysis method including the steps of casting X-rays onto a sample whose principal component is an organic substance with a known molecular formula, and determining the quantity of each contained component other than the principal component in the sample by using the result of a measurement of X-rays emitted from the sample, the method further including the steps of:

a) determining the kind of the contained component based on the energy of the fluorescent X-rays detected in the measurement;

b) setting a quantitative value of the contained component, based on a measured value of the intensity of the fluorescent X-rays from the sample;

c) calculating an area occupancy ratio which represents the proportion of the X-rays falling onto the sample, based on a measured value of the intensity of scattered X-rays from the sample and a theoretical value of the intensity of the scattered X-rays calculated on the assumption that the sample is composed of the principal component and that the entire amount of the cast X-rays fall onto the sample;

d) recalculating the quantitative value of the contained component based on the result of a comparison of the measured value of the intensity of the fluorescent X-rays with a theoretical value of the intensity of the fluorescent X-rays calculated using the quantitative value of the contained component and the area occupancy ratio;

e) recalculating the area occupancy ratio based on the result of a comparison of the measured value of the intensity of the scattered X-rays with a theoretical value of the intensity of the scattered X-rays calculated using the recalculated quantitative value of the contained component and the area occupancy ratio; and f) repeating the recalculation of the quantitative value of the contained component and the recalculation of the area occupancy ratio, and determining the recalculated quantitative value as the definite quantitative value of the contained component when the recalculated quantitative value and/or the recalculated area occupancy ratio satisfies a previously set convergence condition.

As the scattered X-rays, Compton-scattered X-rays or Rayleigh-scattered X-rays, which are generated by scattering of characteristic X-rays emitted from the target of the X-ray-tube on the sample, are typically used, although any kind of X-rays can be used as long as their intensity changes with the size of the region irradiated with the X-rays on the sample. Compton-scattered X-rays or Rayleigh-scattered X-rays, which are generated by scattering of continuous X-rays other than the characteristic X-rays emitted from the target of the X-ray tube on the sample, can also be used.

In principle, the X-ray fluorescence analysis method according to the present invention is used for the quantitative determination of the components contained in a sample having a known thickness. If the thickness of the sample is unknown, the quantitative determination of the components contained in the sample can be performed after the thickness of the sample is estimated by a theoretical calculation based on the ratio of the intensities of the scattered radiations with different levels of energy. One example of the scattered radiations with different levels of energy is the RhK-alpha and RhL-alpha radiations, which are the scattered radiations of the X-rays which occur when rhodium is used as the target material.

In the X-ray fluorescence analysis method according to the present invention, the area occupancy ratio is calculated by comparing a measured value of the scattered X-ray intensity and a theoretical value of the total intensity of the scattered X-rays calculated on the assumption that the entire amount of X-rays are effectively cast onto the sample. The area occupancy ratio is used in the calculation of the theoretical value of the fluorescent X-ray intensity to correct the fluorescent X-ray intensity which varies depending on the sample shape. The quantitative value of a contained component is determined by making the area occupancy ratio and the quantitative value of the contained component converge so that both the theoretical value of the scattered X-ray intensity and that of the fluorescent X-ray intensity will be consistent with their respective measurement values. Therefore, the quantities of the components contained in the sample can be accurately determined without being affected by the shape of the sample.

Another aspect of the present invention developed for solving the previously described problem is an X-ray fluorescence analysis system for casting X-rays onto a sample whose principal component is an organic substance with a known molecular formula and for determining the quantity of each contained component other than the principal component in the sample by using the result of a measurement of X-rays emitted from the sample, the system further including:

a) a contained component determiner for determining the kind of the contained component based on the energy of the fluorescent X-rays detected in the measurement;

b) a quantitative value setter for setting a quantitative value of the contained component, based on a measured value of the intensity of the fluorescent X-rays from the sample;

c) an area occupancy ratio calculator for calculating an area occupancy ratio which represents the proportion of the X-rays falling onto the sample, based on a measured value of the intensity of scattered X-rays from the sample and a theoretical value of the intensity of the scattered X-rays calculated on the assumption that the sample is composed of the principal component and that the entire amount of the cast X-rays fall onto the sample;

d) a quantitative value recalculator for recalculating the quantitative value of the contained component based on the result of a comparison of the measured value of the intensity of the fluorescent X-rays with a theoretical value of the intensity of the fluorescent X-rays calculated using the quantitative value of the contained component and the area occupancy ratio;

e) an area occupancy ratio recalculator for recalculating the area occupancy ratio based on the result of a comparison of the measured value of the intensity of the scattered X-rays with a theoretical value of the intensity of the scattered X-rays calculated using the recalculated quantitative value of the contained component and the area occupancy ratio; and f) a quantitative value determiner for repeating the calculation by the quantitative value recalculator and the calculation of the area occupancy ratio recalculator, and for determining the recalculated quantitative value as the definite quantitative value of the contained component when the recalculated quantitative value and/or the recalculated area occupancy ratio satisfies a previously set convergence condition.

Advantageous Effects of the Invention

In the X-ray fluorescence analysis method and system according to the present invention, the area occupancy ratio for correcting the fluorescent X-ray intensity which varies depending on the shape of the sample is used to determine the quantity value of a contained component by making the area occupancy ratio and the quantitative value converge so that the theoretical value of the scattered X-ray intensity and that of the fluorescent X-ray intensity will match with their respective measurement values. Therefore, the quantities of the components contained in the sample can be accurately determined without being affected by the shape of the sample.

BRIEF DESCRIPTION OF DRAWINGS

FIG. 1 is a configuration diagram showing the main components of one example of the X-ray fluorescence analysis system used in the X-ray fluorescence analysis method according to the present invention.

FIG. 2 is a flowchart illustrating the analysis procedure in one embodiment of the X-ray fluorescence analysis method according to the present invention.

FIGS. 3A and 3B show examples of the samples to which the X-ray fluorescence analysis method according to the present invention can be suitably applied.

FIG. 4 is a table showing the result of a quantitative determination of the components contained in a sample conducted by using the X-ray fluorescence analysis method of the present embodiment.

DESCRIPTION OF EMBODIMENTS

One example of the X-ray fluorescence analysis system used in the X-ray fluorescence analysis method according to the present invention is described. In the present embodiment, the sample is a resin product having a known thickness. The quantitative determination is to be performed for a resin component which is the principal component with a known molecular formula as well as one or more kinds of components contained in the sample other than the resin component (those components are hereinafter simply called the "contained components"). FIG. 1 shows the configuration of the main components of the system.

In FIG. 1, under the control of the control unit 15, excitation X-rays are emitted from the X-ray tube 1 with rhodium (Rh) as the target material and strike the sample 2, whereupon the sample 2 is excited by the excitation X-rays and emits fluorescent X-rays, which enter the X-ray detector 3 (e.g. a lithium-drifted silicon detector), to be thereby detected in the form of an electric current. A portion of the excitation X-rays which have struck the sample 2 are scattered by the sample 2. Those scattered X-rays are also detected by the X-ray detector 3. The detected electric current signals are accumulated within the X-ray detector 3. The accumulation is reset after a predetermined period of time has passed. Consequently, the output signal of the X-ray detector 3 will be a pulsed current signal having a step-like form. The height of each step in this signal corresponds to the energy of one element contained in the sample 2. This pulsed current signal is sent to the preamplifier 4, and further to the proportional amplifier 5 which includes a wave-shaping circuit, whereby the signal is shaped into a series of pulses in an appropriate form, with each pulse having a pulse height corresponding to the height of one of the steps.

The analogue-to-digital converter (ADC) 6 samples and digitizes the pulsed analogue signal at a predetermined sampling period. The multichannel analyzer (MCA) 7 classifies the pulses according to the wave heights of the digitized pulse signals, counts the number of pulses for each classification, creates a wave-height distribution chart, i.e. the X-ray spectrum, and sends it to the data processing unit 10. The data which constitute the X-ray spectrum are stored in the storage section 11.

On the X-ray spectrum, a spectral line specific to each element contained in the sample being analyzed appears in the form of a peak at a position corresponding to the energy value of the fluorescent X-rays emitted from that element. The peaks of the spectral lines of the Rayleigh-scattered X-rays and Compton-scattered X-rays which are generated by scattering of the excitation X-rays on the sample also appear. In the data processing unit 10, the peak extractor 12 reads from the storage section 11 the data which constitute the X-ray spectrum, detects each peak on the X-ray spectrum, and stores the energy value and intensity value of each peak into the storage section 11. Subsequently, the quantitative calculator 13 determines the kind of contained element and its quantity from the energy value and intensity value of each peak. Details of the identification and quantitative determination of the contained elements by the quantitative calculator 13 will be described later.

The quantitative calculator 13 conducts the X-ray fluorescence analysis by the previously described fundamental parameter (FP) method. In the FP method, the content of the principal component (in the present embodiment, the resin component) and those of the other contained components are initially assumed. The quantities of the contained components are determined by repeating the steps of calculating a theoretical intensity of the fluorescent X-rays from the assumed contents, comparing the theoretical intensity with a measured intensity, and modifying the assumed contents based on the difference between the two intensities. In the FP method, the quantitative value of each component is indicated in weight percentage.

As for the fluorescent X-ray intensity, it is commonly known that the measured intensity M and the theoretical intensity T calculated by a theoretical formula have the relationship expressed by the following equation (1):

$$M = kT \quad (1)$$

where k is the coefficient called the "sensitivity factor". The sensitivity factor is previously computed based on the result of an actual measurement of a sample of a pure substance and other information, and stored in the storage section 11.

The X-ray fluorescence analysis conducted by the quantitative calculator 13 of the present embodiment is hereinafter described with reference to the flowchart of FIG. 2. The quantitative calculator 13 includes a contained component determiner 131, quantitative value setter 132, area occupancy ratio calculator 133, quantitative value recalculator 134, area occupancy ratio recalculator 135, and quantitative value determiner 136. As will be described later, the quantitative value setter 132 and the quantitative value recalculator 134, or the area occupancy ratio calculator 133 and the area occupancy ratio recalculator 135 perform similar calculations, and therefore, can be configured as a single calculator, such as a contained component calculator or a single area occupancy ratio calculator.

When a command for initiating the analysis is given by the user via an operation unit 16, the contained component determiner 131 reads the energy value of each peak which has been extracted and stored in the storage section 11 by the peak extractor 12, and determines the kind of each contained component based on the energy value (Step S1). The quantitative value determiner 132 sets the initial quantitative value for each contained component based on the measured value of the intensity of the peak corresponding to that component (Step S2).

Subsequently, the area occupancy ratio calculator 133 computes a theoretical value of the scattered X-ray intensity on the assumption that the sample is purely made of the resin component (Step S3), and additionally computes the area occupancy ratio from the theoretical value and measured value of the scattered X-ray intensity (Step S4). The area occupancy ratio means the proportion of the area where the sample being analyzed is located within the entire area of the X-ray irradiation window. In other words, the area occupancy ratio is a parameter indicating the proportion of the X-rays incident on the sample among the entire amount of X-rays cast toward the sample. The intensity of the scattered X-rays changes depending on the intensity of the X-rays incident on the sample. Accordingly, it is possible to determine the proportion of the X-rays incident on the sample from the ratio of the theoretical value and measured value of the scattered X-ray intensity.

As the scattered X-rays, Compton-scattered X-rays or Rayleigh-scattered X-rays, which are generated by scattering of characteristic X-rays emitted from the target of the X-ray-tube on the sample, are typically used, although any kind of X-rays can be used as long as their intensity changes with the size of the region irradiated with the X-rays on the sample. Compton-scattered X-rays or Rayleigh-scattered X-rays, which are generated by scattering of continuous X-rays other than the characteristic X-rays emitted from the target of the X-ray tube on the sample, can also be used.

As shown in FIG. 3A, in the case of sample A having a shape which entirely covers the X-ray irradiation window, the area occupancy ratio is 100%. On the other hand, in the case of sample B having a shape which covers only a portion of the X-ray irradiation window as shown in FIG. 3B, the area occupancy ratio has a value which reflects the shape of the sample.

The area occupancy ratio calculator 133 computes a modified sensitivity factor by multiplying the calculated area occupancy ratio by a sensitivity factor which is previously specified for each element (Step S5).

Next, the quantitative value recalculator 134 computes a theoretical value of the fluorescent X-ray intensity, using the initial quantitative values which have been respectively set for the contained components by the quantitative value setter 132 (Step S6), and calculates an estimated value of the fluorescent X-ray intensity by multiplying the theoretical value of the fluorescent X-ray intensity by the aforementioned modified sensitivity factor (Step S7). In this manner, the fluorescent X-ray intensity with the shape of the sample taken into account is estimated. Based on the measured value and estimated value of the fluorescent X-ray intensity, the quantitative value of each contained component is recalculated (Step S8).

After the quantitative values of the contained components are calculated by the quantitative value recalculator 134, the quantitative value determiner 136 determines whether or not the previously specified convergence conditions have been satisfied (Step S9). In the present embodiment, there are two convergence conditions: the latest calculation by the quantitative value recalculator 134 should be the second or later calculation; and for each contained component, the difference between the quantitative value of the contained component obtained by the latest calculation by the quantitative value recalculator 134 and the quantitative value of the same contained component obtained by the second latest calculation by the quantitative value recalculator 134 should be equal to or smaller than a predetermined value. If it is determined by the quantitative value determiner 136 that the convergence conditions have been satisfied ("YES" in Step S9), the quantitative values of the contained components obtained by the latest calculation by the quantitative value recalculator 134 are selected as the definite values.

If it is determined that the convergence conditions have not been satisfied ("NO" in Step S9), the area occupancy ratio recalculator 135 computes the theoretical value of the scattered X-ray intensity using the quantitative values of the contained components obtained by the latest calculation by the quantitative value recalculator 134 (Step S11) and renews the area occupancy ratio calculated earlier in Step S3 (Step S4). From this point on, the previously described processes of Steps S4 through S8 are repeated until it is determined by the quantitative value determiner 136 that the convergence conditions have been satisfied ("YES" in Step S9). It should be noted that, in the previous description of Step S6, the initial quantitative values respectively set for the contained components were used to calculate the theoretical intensity, since it was the first calculation by the quantitative value recalculator 134. In the second and subsequent calculations, the quantitative values of the contained components which have already been calculated by the quantitative value recalculator 134 are used to calculate the theoretical value of the fluorescent X-ray intensity.

In the X-ray fluorescence analysis method according to the present embodiment, the area occupancy ratio is calculated from the theoretical value and measured value of the scattered X-ray intensity, and the modified sensitivity factor is calculated using the area occupancy ratio. This prevents the problem that, in the case where only a portion of the cast X-rays falls onto the sample, the quantity values of the contained components will be estimated at lower values than the actual values, since the intensity of the fluorescent X-rays emitted from the sample becomes lower than in the case where the entire amount of cast X-rays fall onto the sample. Therefore, the quantities of the components contained in the sample can be accurately determined without being affected by the shape of the sample.

It is possible to install a camera within the sample chamber to take an image of the sample placed on the X-ray irradiation window in order to recognize the shape of the sample being analyzed and calculate the area occupancy ratio. However, the addition of the camera to the X-ray analysis system makes the system larger and more expensive. Furthermore, if the sample has a glossy surface, it is difficult to determine the aforementioned ratio from an image taken with the camera.

By contrast, with the method and system of the present embodiment, it is possible to avoid the influence of the shape of the sample (inclusive of its thickness) and accurately determine the quantities of the contained components in the sample, without using a camera or similar imaging device.

EXAMPLE

Hereinafter described is the result of a quantitative determination of the contained components performed for the following two samples using the previously described X-ray fluorescence analysis method: Sample 1 having a shape which entirely covers the X-ray irradiation window, and Sample 2 having a shape which covers one half of the X-ray irradiation window. The difference between Samples 1 and 2 only exits in their shapes; they are identical in thickness as well as in the kinds and contents of the contained components.

FIG. 4 shows the result of the quantity determination by the X-ray fluorescence analysis method of the present embodiment ("Corrected") and that of the quantity determination by a conventional X-ray fluorescence analysis method ("Not Corrected"). As can be seen, since the intensities of the fluorescent X-rays from Sample 2 are lower than those of the fluorescent X-rays from Sample 1, the quantitative value of each contained component determined by the conventional method is lower than the actual content, so that the quantitative value of the principal component (resin component), which is calculated by subtracting those quantitative values, is higher than the actual content. By comparison, in the case of the analysis performed by the method of the present embodiment, the quantitative values are properly obtained.

It should be noted that the previous embodiment is a mere example of the present invention and can be appropriately changed within the spirit of the present invention.

In the previously described embodiment, it is assumed that the principal component of the sample is a resin component. Other kinds of samples whose principal component is an organic substance having a known molecular formula (e.g. foodstuffs) can also be analyzed.

In the previously described embodiment, the quantitative value setter 132, area occupancy ratio calculator 133, quantitative value recalculator 134, and area occupancy ratio recalculator 134 are configured as independent components. However, the quantitative value setter 132 and the quantitative value recalculator 134, or the area occupancy ratio calculator 133 and the area occupancy ratio recalculator 135, which perform similar calculations, may be configured as a single calculator.

In the calculation process described in the previous embodiment, the steps which can be performed in parallel may be executed in a different order.

In the previous embodiment, as one convergence condition, it is required that the difference between the quantitative value calculated by the quantitative value recalculator and the previously calculated quantitative value should be equal to or smaller than a predetermined value. Other conditions are also imaginable: For example, it is possible to specify a convergence condition based on the change in the value of the area occupancy ratio, or to include the convergence condition that the difference between the estimated value and measured value of the fluorescent X-ray intensity should be equal to or smaller than a predetermined value.

The previously described embodiment is concerned with the case of performing a measurement on a sample having a known thickness. If the thickness of the sample is unknown, the thickness of the sample can be estimated by a theoretical calculation based on the ratio of the intensities of the scattered radiations with different levels of energy. For example, the RhK-alpha and RhL-alpha radiations which appear on the X-ray spectrum can be used as the scattered radiations with different levels of energy.

REFERENCE SIGNS LIST

1 . . . X-Ray Tube
2 . . . Sample
3 . . . X-Ray Detector
4 . . . Preamplifier
5 . . . Proportional Amplifier
6 . . . Analogue-to-Digital Converter
7 . . . Multichannel Analyzer
10 . . . Data Processing Unit
11 . . . Storage Section
12 . . . Peak Extractor
13 . . . Quantitative Calculator
131 . . . Contained Component Determiner
132 . . . Quantitative Value Setter
133 . . . Area Occupancy Ratio Calculator
134 . . . Quantitative Value Recalculator
135 . . . Area Occupancy Ratio Recalculator
136 . . . Quantitative Value Determiner
15 . . . Control Unit
16 . . . Operation Unit

The invention claimed is:

1. An X-ray fluorescence analysis method including steps of casting X-rays onto a sample whose principal component is an organic substance with a known molecular formula, and determining a quantity of each contained component other than the principal component in the sample by using a result of a measurement of X-rays emitted from the sample, the method further comprising steps of:
 a) determining a kind of the contained component based on an energy of the fluorescent X-rays detected in the measurement;
 b) setting a quantitative value of the contained component, based on a measured value of an intensity of the fluorescent X-rays from the sample;
 c) calculating an area occupancy ratio which represents a proportion of the X-rays falling onto the sample, based on a measured value of an intensity of scattered X-rays from the sample and a theoretical value of the intensity of the scattered X-rays calculated on an assumption that the sample is composed of the principal component and that an entire amount of the cast X-rays fall onto the sample;
 d) recalculating the quantitative value of the contained component based on a result of a comparison of the measured value of the intensity of the fluorescent X-rays with a theoretical value of the intensity of the fluorescent X-rays calculated using the quantitative value of the contained component and the area occupancy ratio;
 e) recalculating the area occupancy ratio based on a result of a comparison of the measured value of the intensity of the scattered X-rays with a theoretical value of the intensity of the scattered X-rays calculated using the recalculated quantitative value of the contained component and the area occupancy ratio; and
 f) repeating the recalculation of the quantitative value of the contained component and the recalculation of the area occupancy ratio, and determining the recalculated quantitative value as a definite quantitative value of the contained component when the recalculated quantitative value and/or the recalculated area occupancy ratio satisfies a previously set convergence condition.

2. An X-ray fluorescence analysis system for casting X-rays onto a sample whose principal component is an organic substance with a known molecular formula and for determining a quantity of each contained component other than the principal component in the sample by using a result of a measurement of X-rays emitted from the sample, the system further comprising:
 a) a contained component determiner for determining a kind of the contained component based on an energy of the fluorescent X-rays detected in the measurement;
 b) a quantitative value setter for setting a quantitative value of the contained component, based on a measured value of an intensity of the fluorescent X-rays from the sample;
 c) an area occupancy ratio calculator for calculating an area occupancy ratio which represents a proportion of the X-rays falling onto the sample, based on a measured value of an intensity of scattered X-rays from the sample and a theoretical value of the intensity of the scattered X-rays calculated on an assumption that the sample is composed of the principal component and that an entire amount of the cast X-rays fall onto the sample;
 d) a quantitative value recalculator for recalculating the quantitative value of the contained component based on a result of a comparison of the measured value of the intensity of the fluorescent X-rays with a theoretical value of the intensity of the fluorescent X-rays calculated using the quantitative value of the contained component and the area occupancy ratio;
 e) an area occupancy ratio recalculator for recalculating the area occupancy ratio based on a result of a comparison of the measured value of the intensity of the scattered X-rays with a theoretical value of the intensity of the scattered X-rays calculated using the recalculated quantitative value of the contained component and the area occupancy ratio; and
 f) a quantitative value determiner for repeating the calculation by the quantitative value recalculator and the calculation of the area occupancy ratio recalculator, and for determining the recalculated quantitative value as a definite quantitative value of the contained component when the recalculated quantitative value and/or the recalculated area occupancy ratio satisfies a previously set convergence condition.

* * * * *